United States Patent [19]

Parekh et al.

[11] Patent Number: 5,422,079
[45] Date of Patent: Jun. 6, 1995

[54] AUTOMATED PROCESS EQUIPMENT

[75] Inventors: Rajesh B. Parekh, Kirtlington; Anthony H. Merry, Charlbury; James Bruce, Eynsham; Antonis C. Ioannides, Sittingbourne; Albert E. Platt, Abingdon, all of United Kingdom

[73] Assignee: Oxford Glycosystems Limited, Abingdon, England

[21] Appl. No.: 159,507

[22] Filed: Nov. 30, 1993

Related U.S. Application Data

[63] Continuation-in-part of Ser. No. 719,289, Jun. 21, 1991, abandoned.

[30] Foreign Application Priority Data

| Jun. 21, 1990 | [GB] | United Kingdom | 9013828 |
| Jun. 21, 1990 | [GB] | United Kingdom | 9013830 |
| Jun. 21, 1990 | [GB] | United Kingdom | 9013831 |
| Mar. 27, 1991 | [GB] | United Kingdom | 9106489 |

[51] Int. Cl.⁶ .................................................. G01N 33/00
[52] U.S. Cl. ........................................ 422/129; 435/291
[58] Field of Search .............. 436/53, 52; 435/291; 422/63-67, 129

[56] References Cited

U.S. PATENT DOCUMENTS

| 4,052,161 | 10/1977 | Atwood et al. |  |
| 4,312,635 | 1/1982 | Carlisle. |  |
| 4,520,108 | 5/1985 | Yoshida et al. |  |
| 4,865,811 | 9/1989 | Newton et al. | 436/53 |
| 4,912,051 | 3/1990 | Zaromb | 436/53 |
| 5,108,928 | 4/1992 | Menard et al. | 436/53 |

FOREIGN PATENT DOCUMENTS

| 0149163 | 7/1985 | European Pat. Off. |
| 0215766 | 3/1987 | European Pat. Off. |
| 0249932 | 12/1987 | European Pat. Off. |
| 63-91559 | 4/1988 | Japan. |
| 63-91561 | 4/1988 | Japan. |
| 63-91562 | 4/1988 | Japan. |

OTHER PUBLICATIONS

"Carbohydrate Structure of Vesicular Stomatitis Virus Glycoprotein," Reading et al., *Journal of Biological Chemistry*, vol. 253, No. 16, Aug. 1978.

"Purification of Oligosaccharides Having a Free Reducing-End from Glycopeptide Sources," Bendiak et al., *Carbohydrate Research*, vol. 151, Elsevier Science Publishers B.V., 1986.

*Primary Examiner*—Timothy M. McMahon
*Attorney, Agent, or Firm*—Nixon & Vanderhye

[57] ABSTRACT

An instrument that is particularly designed for the automatic release and isolation saccharides from glycoconjugates comprises a source of inert gas that can be passed along a line, to bring together all the required reagents with the sample, heat the sample in the presence of the reagents for the required time and at the required temperature, pass the resultant mixtures through chromatographic columns, and deliver the separated material to a collection point. The release and separation can be conducted on two samples of glycoconjugate simultaneously, even when the samples are of different glycoconjugates requiring different processing parameters. The material of one sample can be prevented from mixing with or otherwise contaminating the material of the other sample.

14 Claims, 9 Drawing Sheets

AUTOMATED PROCESS EQUIPMENT

RELATED TO EARLIER APPLICATION

This application is a continuation-in-part of our application Ser. No. 07/719,289, filed Jun. 21, 1991, now abandoned.

FIELD OF THE INVENTION

This invention relates to apparatus for automatically performing a sequence of chemical/physical processes, in particular the release reactions and purification procedures that may be used to isolate saccharides from glycoconjugates.

BACKGROUND OF THE INVENTION

The analysis of glycoconjugates is of increasing importance. This can be done by releasing the constituent glycans, and determining the relative amounts of the glycans. The most accurate and quickest analysis depends on obtaining the quantitative release of glycans, in intact form, preferably from a number of samples simultaneously.

Glycans can be released from glycoconjugates by the action of hydrazine. In addition to various descriptions in the literature, which give poor yields of intact glycans, in general, this reaction is the subject of U.S. Pat. Nos. 4,719,294 and 4,736,022 (Rademacher et al) and European Patent Publications Nos. 462,796, 462,797 and 462,798, two of which correspond to commonly-assigned copending U.S. applications, one having the Ser. No. 08/32,166, both filed Mar. 12, 1993. The contents of all these descriptions are incorporated by reference.

U.S. Pat. No. 4,052,161, issued Oct. 4, 1977, to Atwood et al, describes a kinetic analyser. It depends on various pipetting steps, and a number of mechanically-acting parts.

An object of the present invention is to provide apparatus for automatically subjecting a glycoconjugate to conditions under which recovery or release, or both, of an N-glycan or an O-glycan, or both, from the glycoconjugate is performed.

SUMMARY OF THE INVENTION

Briefly, the novel apparatus comprises means for automatically subjecting the glycoconjugate to the influence of a suitable reagent and means for automatically controlling the conditions under which the glycoconjugate is subjected to the influence of the reagent in such a way as to allow subsequent recovery of the glycan in a form separate from the conjugate material. More particularly, the apparatus comprises:

a source of inert gas;

a line into which the inert gas can pass, under pressure, to a plurality of outlets, the line being sealed with respect to the atmosphere; and, in successive connection with the line via appropriate valves:

a plurality of vessels for liquid reactants that can be introduced into the line by selective direction of the inert gas therethrough; and at least one reaction chambers into which said liquid reactants can be selectively directed and from which reaction products can pass along the line;

the apparatus further comprising at least one liquid flow detector selected from a first liquid flow detector for detecting liquid flow in the line between said vessels and said reaction chamber, and a second liquid flow detector for detecting liquid flow between said at least one reaction chamber and one or more of said outlets.

As described in more detail below, apparatus of the invention permits the following:

To perform measured liquid deliveries under gaseous pressure, to perform path cleaning operations in order to minimise contaminations, to maintain anhydrous reaction conditions, to mix reagents in accurately determined ratios, either in liquid flow or in a vessel, to perform chemical reactions both by exposing an immobilised substrate to a flow of reagent and by delivering reagents to a vessel containing the substrate. Some of these reactions involve exposing the holding vessel to precisely controlled, non-ambient temperatures and to this end a device is included to perform this temperature control and to regulate the rate of change of temperature. A further object is to deliver purified saccharides to a predetermined delivery point.

The invention comprises broadly a system maintained under an essentially oxygen-free and moisture-free environment achieved by the use of an inert gas, at least one reaction vessel into which a sample is placed initially, plus intermediate holding vessels which can be used for subsequent derivations of the substrate. These vessels are positioned in such a manner as to permit deliveries of liquid from one vessel to another either via a column or a cartridge of columns or directly. This transfer may be carried out several times. Means are provided for the pressurisation and ventilation of the vessels. These are so constructed as to facilitate complete washing of the assembly. A feature of the invention is that the apparatus can perform operations on two or more reaction vessels if required at the same time, each containing a different sample of glycoconjugate, in a manner which results in the minimum of cross-contamination, and the minimum in variation between each reaction vessel.

The apparatus has the ability to operate in a variety of modes in order to recover saccharides in an unmodified, unreduced form. Such modes can include procedures which result in the selective recovery of N-linked type or O-linked type saccharides or both.

The apparatus may also include one or more of: an assembly of purification media which effect the required purification processes, a pressure regulator to maintain a constant working pressure, a restrictor in order to provide a slow flow rate of gas at various points in the process.

The apparatus also comprises heaters for the holding vessels. These may include a means of being automatically raised up to surround and enclose the holding vessels during the temperature control process, and to be automatically lowered at other points in the process. Such means may constitute an independent aspect of the invention described herein.

A controller to perform the automated switching of valves, timing, control of temperature and the monitoring of liquid detectors, is also provided.

BRIEF DESCRIPTION OF THE DRAWINGS

The invention will now be described, by way of example only, with reference to the accompanying drawing, in which.

DETAILED DESCRIPTION OF THE INVENTION

Figure 1A:
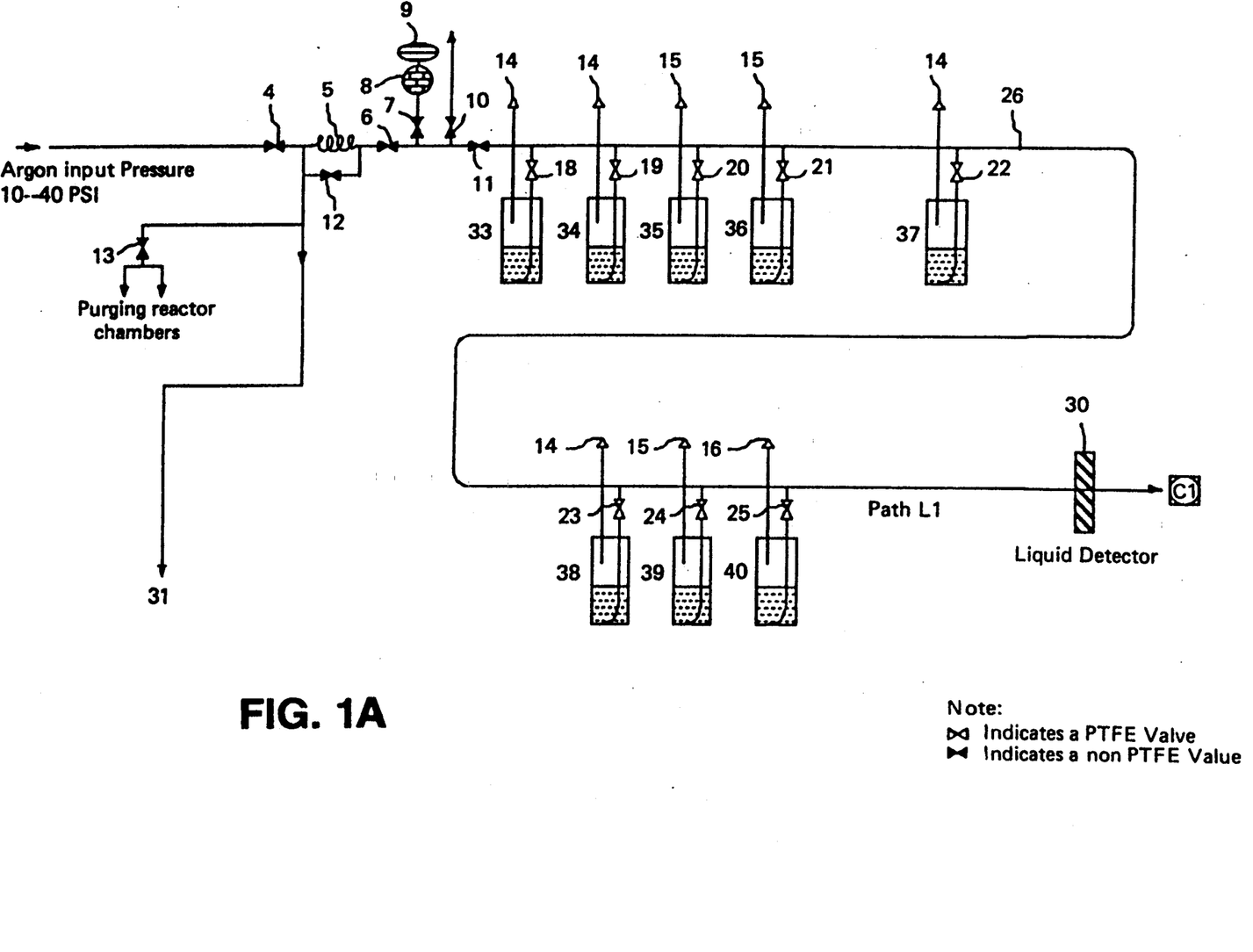
FIGS. 1a and 1b show a diagram of apparatus embodying the present invention.
Figure 1B:
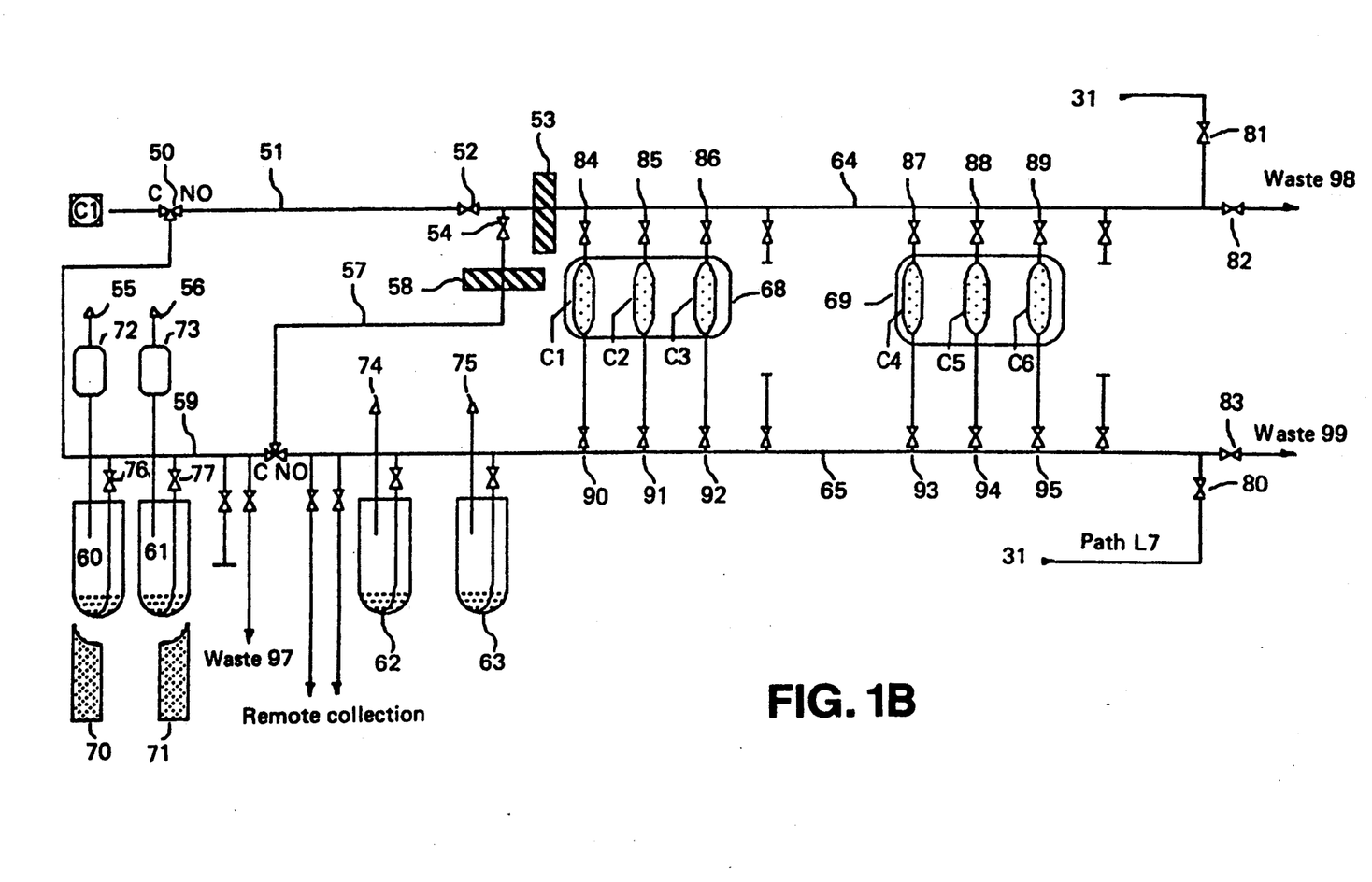

Referring now to FIG. 1, the apparatus is in the form of an instrument which contains equipment capable of simultaneously operating on two separate glycoconjugate samples to release automatically the respective saccharides from the glycoconjugates and to isolate each of the saccharide materials. There are two reaction vessels 60, 61, each arranged to hold a sample and to work with a respective heater 70, 71 and a respective set of chromatographic columns 68 (C1, C2 & C3), 69 (C4, C5 & C6) and a respective holding vessel 62, 63. Reagents from a common set of reagent bottles 33 through 40, can be supplied to each sample. The instrument can be programmed to carry out different processes on each sample at the same time and to provide the most appropriate set of conditions for the release of saccharide from glycoconjugate and for the isolation of the saccharide material, without the materials of one sample mixing or contaminating the other and whilst both samples use common connections and valves, again without contamination occurring.

Reservoirs 33 through 40 contain different reagents which, as mentioned above, can be used in the operations on either 5 sample:. For example, their contents may be as follows:

Reservoir 33—water
Reservoir 34—ethanol
Reservoir 35—acetic anhydride
Reservoir 36—BE, i.e. butanol/ethanol (4:1)
Reservoir 37—sodium acetate (0.2M)+NaOH, to pH 8
Reservoir 38—copper acetate (0.1M in acetic acid)
Reservoir 39—BE
Reservoir 40—hydrazine (distilled, <0.5% water)

The apparatus has a supply of input inert gas which, for the purpose of illustration only, is argon. The supply is connected via a regulator (not shown) to a set of valves 14, 15 and 16, which act to pressurise or ventilate the reservoirs 33 through 40 in order to make deliveries of the reagents as described below. Valve 14 is connected to reservoirs 33, 34, 37 and 38, valve 15 is connected to reservoirs 35.36 and 39, and valve 16 is connected only to reservoir 40. This arrangement isolates any reagents which are incompatible.

The argon gas supply enters along line 26, passing through valve 4, flow restrictor 5, valve 6 and valve 11 to the instrument. The argon supply communicates through a filter 8 with a pressure transducer 9 when valve 7 is open. A valve 10 can be used to vent gas from the parts of the system upstream of valve 11, so that when liquid is required to be pushed along the line 26 to a destination, the build-up of pressure can be made gradual by closing valve 10 and opening valve 11. Flow restrictor 5 can be by-passed by opening a valve 12.

Valve 13 can be opened to deliver argon to the area surrounding the reaction chambers when the reaction vessels are being fitted 60 as to 5 exclude air as far as possible. Waste is collected in a waste bottle (not shown) and argon is supplied along line 31 to this waste bottle. The instrument performs a series of steps (in the sequence A to L), which are described in detail below, and which can be summarised:

A—Instrument checks
B—Inert Gas Purge
C—Hydrazine Delivery
D—Hydrazine Reaction
E—Hydrazine removal
F—Re-N-Acetylation
G—Conjugate Removal
H—Elution
I—Desalting/acetohydrazone cleavage (i)
J—Acetohydrazone cleavage (ii)
K—Collection
L—System wash

A) Instrument Checks

At start-up, the instrument performs a number of self-tests:

a) To check that the heater controller is functioning, the control temperature for both reaction vessels 60, 61 is set at a temperature above ambient, and is held there for the duration of the self-test.

b) In order to check the source inert gas pressure, valve 10 is opened to vent the system. Valve 10 is then closed and valve 7 opened, and after a preset time, the pressure is read. A low reading will cause the controller to register an error, and indicate a low inert gas pressure. Any other reading, outside an allowable working range, will cause the controller to communicate to the user to alter the pressure to 6 psi and restart the test.

The low reading is set to 1 psi, and the allowable working range is set to 6±0.5 psi.

c) In order to check that there are no leaks in the lines/valves in the main liquid transfer line, initially valves 11, 52 and 54 are opened. The pressure transducer 9 should register between the limits set above. If not, then the controller will register an error and stop the test and all valves will be closed, shutting off the main inert gas supply. After a time interval, the pressure is read, and if this pressure has dropped significantly (typically by >0.2 psi), an error is again registered and the controller will stop the test.

Valve 82 is now opened to open a vent to waste, and after a preset time, the pressure is checked. If this is above a set limit (typically 1 psi), then this indicates that there is a blockage and the controller will again shut down the instrument. The above procedure is then repeated, this time using valve 83 instead of valve 82. The measurements provided by the pressure transducer 9 are used to ensure that each valve is performing to specification.

d) In order to check that the liquid reservoir and reservoir valves are leak-tight, the reservoirs are pressurised to working pressure and, in turn, valves 14, 15 and 16 are opened. In each case the time taken for the pressure to reach a preset percentage of the working pressure (typically 60%) is recorded. If this time exceeds a preset limit, then the controller will register a gas leak/bottle missing error. The gas is shut off and after a preset time the pressure is read. If this has dropped significantly (typically by >0.2 psi) then an error is flagged.

The above procedure is repeated with the holding-/collection vessels 62, 63.

All deliveries to waste go to a waste bottle which is not specifically shown. This waste bottle is checked in the same manner as above and also the time taken to pressurise it to 63% of the supply pressure is used to give an indication as to how full it is.

e) To ensure that the chromatographic assemblies are in place, valves 52, 81, 84, 85, 86, 90, 91, 92 and 80 are opened and the time taken for the pressure to reach a percentage (typically 60%) of the working pressure is recorded. If this time exceeds a preset value then the user is warned to check that the columns are in place. The gas supply is cut off and the pressure checked after a preset time. If the pressure has dropped significantly (typically by >0.2 psi) then an error is flagged. Valves 82 and 83 are opened to vent the system and the pressure checked again.

If this is above a certain limit (typically ~1 psi) then an error is flagged. This is repeated for the second set of columns if the second reaction vessel 61 is to be used.

In addition, opto-sensors (not shown) are used to ensure that the correct set of columns in their cartridge, have been fitted.

f) To ensure that the heater drive is operating the heaters 70, 71 are driven up and down. The temperatures of the heater blocks are now checked to be within an allowable range (typically ±2° C.) of the set temperature. If not then the test is halted.

This completes the instrument checks.

The further operation of the instrument is now described as it applies to one sample only. The sample of glycoconjugate which is to be processed by the instrument is first dialysed and freeze-dried in reaction vessel 60 which is then screwed on to the instrument.

B) Inert Gas Purge

Inert gas is passed through reaction vessel 60 for 1 minute in order to purge the sample and to eliminate air and moisture from the reaction vessel.

C) Hydrazine Delivery

This step is carried out in order to deliver the required volume of pure, anhydrous hydrazine to the sample.

Prior to delivering the hydrazine to the reaction vessel, the lines are cleaned in accordance with the line-cleaning procedure outlined below. 2 lots of 100 μl hydrazine are delivered using type A deliveries (see below for descriptions of each delivery type) to waste. Hydrazine is then delivered to the reaction vessel, again using a type A delivery of 100 μl. To eliminate hydrazine from the lines, water is then delivered (type E) via line 59 to waste 97, and then via lines 51 and 57 to waste 97.

D) Hydrazine Reaction

This step is carried out in order to expose the sample to a predetermined temperature cycle to cause reaction with the hydrazine, thereby cleaving the saccharides from the parent glycoconjugate, whilst maintaining anhydrous conditions within the reaction vessel.

The parameters to be set for the hydrazine reaction are the rate of the temperature rise, the temperature at which the reaction vessel is to be held during the reaction, and the duration of this reaction, and these depend on the particular sample being processed. These parameters are entered into the instrument controller by the user.

Initially, the heater 70 is physically raised to surround the reaction vessel 60, and the instrument controller initiates the temperature rise needed to produce the required temperature profile in the reaction vessel 60. During the temperature rise, chamber 72 is vented to prevent a build-up of pressure inside the reaction vessel. When the peak temperature is reached, chamber 72 is closed and the controller then maintains the temperature for the required time. During this reaction process, column washing can take place. The purpose of this process is to render the columns and column materials finally free of any acquired contaminants, and also to equilibrate the binding material of the columns in the appropriate solvent composition. The following procedure is used:

6 ml water is delivered (type A) via line 51 to column C1 and to waste 99, and then 3 ml water is delivered to columns C2 and C3 to waste 97. 6 ml BE is then delivered via column C1 to waste 99 (all type A deliveries). A purge with argon after the latter delivery is performed along path 64 to waste 98. This leaves column C1 saturated in BE.

When the reaction time has been completed, the heater is lowered and the control temperature set to ambient. Some time (typically 20 mins) is allowed to elapse before the next step is carried out, to allow the contents of the reaction vessel to cool.

E) Hydrazine Removal

This step is carried out in order to separate the saccharides (in de-N-acetylated, hydrazone form) from the hydrazine, and leaves the saccharides in an immobilised state.

a) 3 ml BE is delivered to the reaction vessel (type F delivery). A liquid mix is then carried out. The contents of the reaction vessel 60 are then transferred to column C1, which contains cellulose. The released saccharides bind to the cellulose in column C1 whilst the hydrazine and surplus butanol/ethanol flow out to waste 99 (type D—delay zero). This process is repeated twice more.

b) In order to render reaction vessel 60, its top assembly and vent chamber 72 free of residual hydrazine to allow subsequent chemistry to be carried out in this vessel, all traces of hydrazine must now be removed. This is done by delivering 6 ml water to the reaction vessel (type F delivery). The water overfills the reaction vessel into a venting chamber 72. A liquid mix is performed and the liquids passed out through waste 97. This is then repeated three times with ethanol. The heater is then raised and the temperature set to 100° C. The heater is set to 50° C. at the beginning of the hydrazine removal process, in order to preheat the assembly. During the heating process, to facilitate removal of solvents, inert gas is blown through the reaction vessel from valve 55 via line 59 to waste 97. This continues for one hour.

F) Re-N-Acetylation

Residual hydrazine is first removed from column C1 by appropriate solvent washing. Any N-acetylable groups on the released non-carbohydrate material are then converted to an N-acetylated form. In this form, this non-carbohydrate material can be separated chromatographically from the saccharides. Partial N-acetylation of the saccharides may also take place.

Solvent washing to remove residual hydrazine is performed by delivering 3 ml ethanol to the reaction vessel 60 (type F), and then passing this from the reactor to column C1 and to waste 99 via line 57 (type D—on 2.5 s, off 2.5 s). This is repeated. For acetylation, 0.4 ml acetic anhydride is delivered (type A) to the reaction vessel 60 along with a volume of BE. The contents are stirred with argon and then passed on to column C1 at a defined flow rate which may allow acetylation of the conjugate.

G) Conjugate Removal

The conjugate may now be separated from the saccharides bound to the cellulose column, by mixing a volume of water with BE again in reaction vessel 60.

a) 0.5 ml water is delivered to reaction vessel 60, followed by 5 ml BE (type F delivery). The contents of the reaction vessel 60 are mixed using inert gas and are then delivered to column C1 and again to waste 99 via line 57 (type D—on 2.5 s, off 2.5 s).

b) A column wash is performed, removing traces of butanol from column C1. This is done by delivering 3 ml of ethanol to the reaction vessel (type F), and then delivering the contents of the reaction vessel to column C1 and to waste 99, via line 57 (type D—on 2.5 s, off 2.5 s). This is then repeated.

In this embodiment release and recovery of the glycan are described. However, it is to be understood that the instrument now described can be set up to perform either release or recovery, or both, of the glycan. In the same way either an N-glycan or an O-glycan can be released or recovered from a glycoconjugate or operations performed simultaneously to release or recovery both N-glycan and O-glycan from a glycoconjugate.

H) Elution

This step is carried out in order to elute the partially re-N-acetylated saccharides from their binding sites, into a vessel, whereupon the re-N-acetylation can be taken to completeness.

a) Inert gas is delivered from valve 81 via column C1, to waste 99, for 1 minute to remove all liquid.

b) Elution is carried out with 0.25 ml sodium acetate delivered to the reaction vessel 60, via line 51, column C1 and line 59 (type A). This is repeated 9 times. Finally, an inert gas purge is done from valve 80, line 65, line 59 to the reaction vessel 60 in order to ensure that none of the sample remains in line.

c) The eluted saccharides in the sodium acetate mixture are acetylated by addition of 0.4 ml acetic anhydride delivered to the reaction vessel 60 (type A). The contents of the reaction vessel 60 are mixed using inert gas and the reaction allowed to continue for 20 minutes.

I) Desalting/acetohydrazone Cleavage (i)

This step is carried out in order to convert the saccharides, which are at present in the acetohydrazone form to the free reducing sugar.

a) The sodium ions present in the re-N-acetylated saccharide mixture are removed by passage through a column of Dowex AG50, or other suitable ion exchange resin, contained in column C2. The contents of the reaction vessel 60 are therefore passed along a path and down through column C2 at which stage sodium ions are exchanged for hydrogen ions. This process also partially cleaves the acetohydrazone derivative of the released saccharides. The saccharides, with partially cleaved acetohydrazone derivatives, are collected in collection vessel 62 after passage through the Dowex column C2. 0.5 ml water is delivered to the reaction vessel 60 (type A), and the first step is repeated.

b) The contents of the collection vessel 62 are delivered to the reaction vessel 60 (type C delivery).

c) 0.5 ml water is delivered to the collection vessel, and the previous step is repeated.

J) Acetohydrasone Cleavage (ii)

This step is carried out in order to drive the acetohydrazone conversion to completeness. This is done by exposing the sample to a mild Lewis acid hydrolysis by delivering 0.3 ml 0.1M copper (II) acetate (0.1M in acetic acid) to the reaction vessel 60 and allowing the reaction to carry on for 1 hour at ambient temperature.

K) Collection

This step is carried out in order to desalt the sample solution and to deliver it to the desired collection point. The contents of the reaction vessel are delivered via path 57 and column C3 to either the 5 collection vessel in the instrument or to a remote collection point. 0.5 ml water is then delivered to the reaction vessel and the previous step is repeated.

L) System Wash 6 ml ethanol is passed through each reaction vessel and the reaction vessels heated to 100° C. Argon is then passed through the reaction vessels to dry them. This step is carried out in order to clean the lines, and to render the reaction vessel, and the associated pressurisation/ventilation system, essentially anhydrous. After this the system should be in a condition such that a subsequent delivery of hydrazine to either reaction vessel, would result in pure, anhydrous hydrazine being delivered.

Delivery of reagents between reservoirs, columns or waste comprises a number of types,

Delivery Type A—Accurate Delivery

This type of delivery is carried out by initially pressurising the source reservoir and activating appropriate valves to open a path to waste. This path includes any detectors to be used in the delivery. Inert gas is purged along this path for a set time in order to expel any droplets of liquid which may interfere with the detector system. The respective valve (18–25, 76–79) connecting the reservoir to the transfer line 51, 57, 59, 64 or 65 is then activated.

The control system of the instrument delivers the volume of liquid required to the required destination via the required flow path.

Delivery type B—continuous

This delivery is used when it is required to deliver the total contents of one reservoir to another, along a path which does not have a liquid detector, e.g. between collection vessel 62 and reaction vessel 60 via path 65.

The parameter specified is the time for which the delivery valve is left open. This time is long enough so that at the lowest working pressure allowed, the total contents are delivered to the destination. As in type A, an initial inert gas purge is done before the delivery begins, but on this occasion, the path is opened to the final destination, rather than to waste.

Delivery type C—continuous

This delivery is similar to type B, but is used when delivering via the chromatographic assemblies 68, 69.

Delivery type D—slow delivery

This delivery is used in the same circumstances as type C, but it delivers the liquid in a series of pulses. The delivery valve is opened for pulse on time and closed for pulse off time. This effectively gives a slower flow rate.

Delivery type E—liquid/inert gas mix

In order to clean the delivery lines after a delivery, volumes of an appropriate solvent are delivered along the lines to waste, interspersed with volumes of inert gas. The water reservoir 33 is positioned furthest from the reaction vessels and chromatographic equipment 80 so that any delivery of water will wash all the liquid lines.

Delivery type F—hybrid delivery

This delivery is used when it is required to deliver quickly, large volumes to the reaction vessel.

After an initial inert gas purge, the path to the destination is opened, and the delivery valve is opened to deliver the required amount of liquid. After delivery, the delivery valve is closed, and the liquid is pushed by the inert gas to the destination.

Detector 30 is placed upstream of valve 50 and is mainly used for small volume deliveries, typically <500 μl to the reaction vessel. Detector 53 is placed between valve 50 and valve 52, as close to valve 52 as possible. This is mainly used for large deliveries (typically >2.5 ml) to the reaction vessel 60 or columns 68.

Detector 58 is placed between valve 96 and valve 54, as close to valve 54 as possible. This is mainly used for deliveries from the reaction vessel to the columns. In the case of delivering a reagent required to be completely free of other reagents, a dummy delivery of this reagent can be carried out, prior to the final delivery. For example, before hydrazine is delivered to the reaction vessel 60, small volumes of hydrazine are delivered from the reservoir and to waste via path 59.

To enable the proper washing of the reaction vessel to eliminate 25 residual hydrazine, the system incorporates chambers 72, 73 allowing the reaction vessels 60, 61 to be overfilled with liquid, the overflow being collected in the chambers 72, 73. These vessels are described in detail later. To ensure that the reaction vessel is completely clean and dry, it is washed with water and ethanol, and is then heated. As it is heated, inert gas is blown through from the pressure/vent line 55, 56 and through to waste.

Valves

The liquid delivery valves used in the instrument comprise valve blocks and individual change-over valves, which act to create paths for liquid delivery. These valves utilise solenoid-operated diaphragms, constructed from materials, such as PTFE, resistant to the chemicals used.

The valve blocks comprise multiple diaphragms, each isolating one port from a common through line. The change-over types utilise the diaphragm to connect between a common (always open) port and one of two other ports. In its deactivated state the path is from the common to the normally open port. When energised, the path is from the common to the normally closed port.

Liquid Detectors

The liquid detectors used in the instrument operate by passing a light beam through the tubing making up the liquid flow path to a photosensor. The detectors detect liquid by recognising the refraction of the light beam caused by the presence of liquid in the tube.

Chromatographic Columns

The chromatographic columns are arranged in two banks, each comprising three columns mounted in a cartridge. The columns are identified diagrammatically in FIG. 1 and in front elevation in FIG. 2, as columns C1 to C3 and columns C4 to C6. Columns C1 to C3 are mounted in a cartridge CT1 and can be used to process one sample, whilst columns C4 to C6 are mounted in a cartridge CT2 and can be used to process another sample. Depending on the separate requirements of the two samples, the contents of columns C1 to C3 can be, respectively, identical to the contents of columns C4 to C6.

The cartridges CT1 and CT2 are blocks of plastic having holes for 5 retaining the columns to facilitate mounting and de-mounting of the columns in the instrument.

Figure 2:
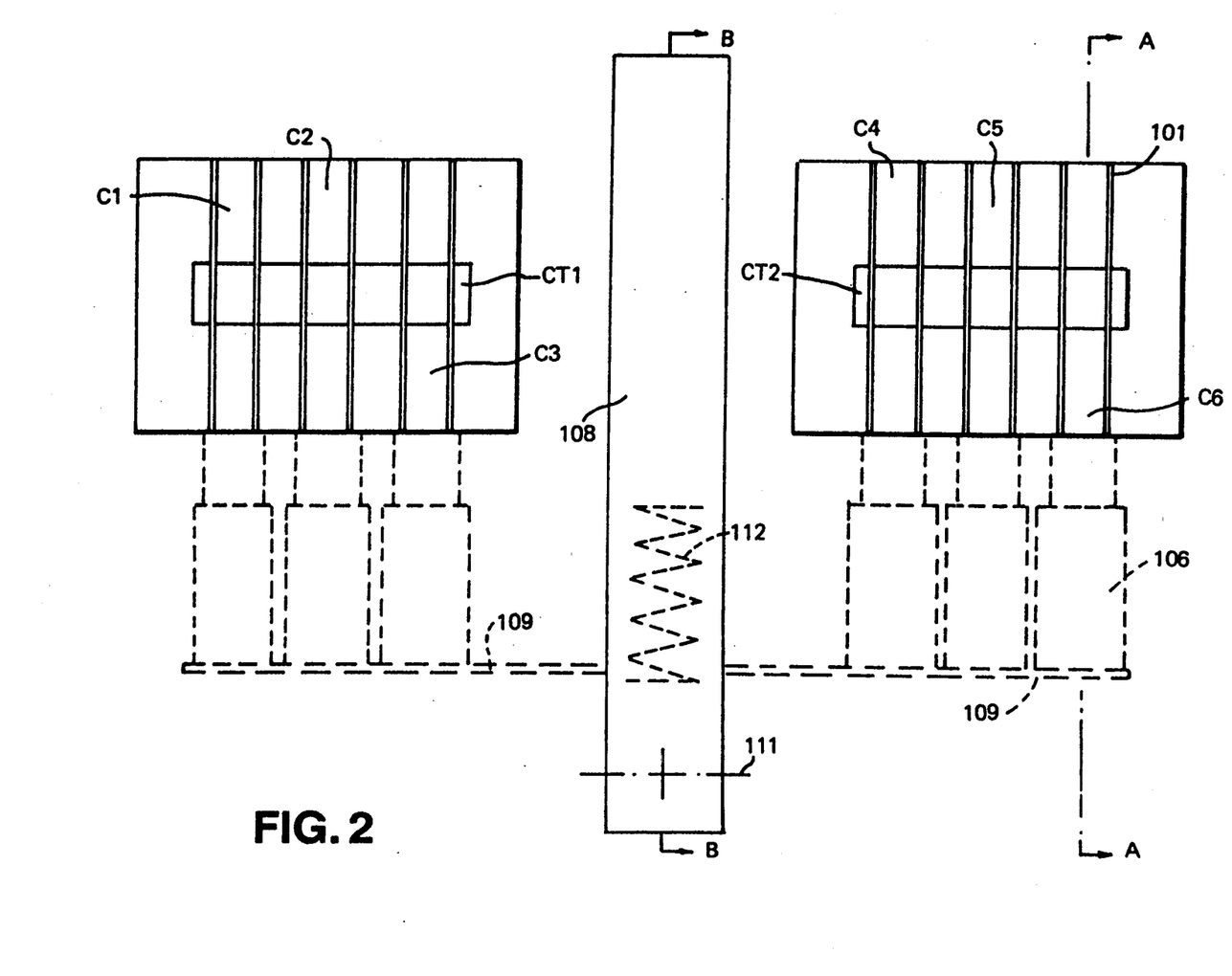
FIG. 2 is a front elevation of the apparatus of FIG. 1, showing two sets of chromatographic column assemblies.

By way of example, columns C1 and C4 are packed with microcrystalline cellulose or other material to which saccharides will bind. Columns C2 and C5 are each in the form of a bed of Dowex AG50 resin (H+ form) which is capable of removing cations from the eluent and also capable of effecting a mild acid hydrolysis of the saccharide. Column C2 may also have C18 silica sited as a bed under the AG50 bed. This material is capable of removing the N-glycopeptide moieties, which are produced in one of the operation modes.

Columns C3 and C6 are each in the form of a mixed bed of Chelex resin (Na+ form) and Dowex AG50 resin (H+ form). This material is capable of exchanging divalent cations for sodium cations and is further capable of removing these sodium cations.

Figure 3:
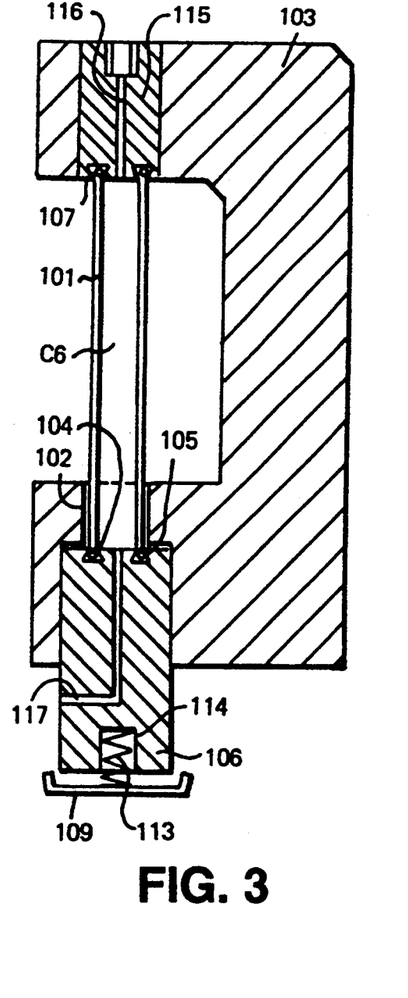
FIG. 3 is a section along the line A—A of FIG. 2.
Figure 4:
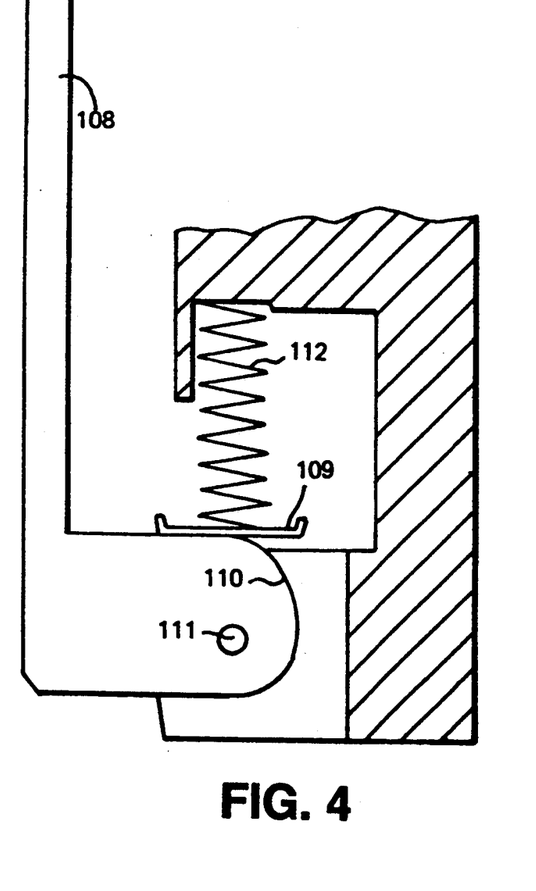
FIG. 4 is a section along the line B—B of FIG. 2.

FIGS. 2, 3 and 4 show the assembly in which the chromatographic 20 columns C1 through C6 are mounted. FIG. 3 is a section through column C6, this column comprising a cylindrical tube 101 made of glass or other suitable material. Tube 101 can be placed in its cartridge along with the tubes for columns C5 and C4. The cartridge is then inserted in the instrument so that column C6 locates in a cylindrical opening 102 in the frame 103 of the instrument, to sit on a lower O-ring 104. The columns C4 to C6 can safely be left in this position as the sides of the openings, such as opening 102, prevent them from falling out.

Referring again to Column C6, O-ring 104 is located in an annular recess 105 in a sliding member 106 and, when member 106 is urged upwards (as described below), tube 101 is additionally brought into contact with an upper O-ring 107, thus sealing the both ends of the tube 101. Sliding member 106 is urged upwards when a lever 108 is swung up into the position shown in FIG. 4. This causes a tray 109, which extends across all six chromatographic columns, to be urged upwards to bring tube 101 into firm contact with the two O-rings 104, 107. The top and bottom ends of all columns C1 to C6 are thus sealed against their respective pairs of O-rings.

As shown in FIG. 4, lever 108 has a surface 110 shaped eccentrically in relation to its pivot axis 111, such that when the lever 108 is rotated into the position shown in FIG. 4, tray 109 is urged upwards against the compression of spring 112, which is positioned in the centre of tray 109 between the two groups of columns C1 to C3 and C4 to C6. In relation to column C6, the movement of lever 108 causes body 106 to be urged to slide upwards in frame 103.

In addition, because there may be slight differences between the individual lengths of the glass tubes of columns C1 to C6, a spring 113, located in a recess 114 in sliding member 106, provides a degree of spring cushion between tray 109 and the compressability of O-rings 104, 107. All six columns are similarly cushioned.

Sliding body 106 and a corresponding insert 115 in frame 103, both have through openings 116, 117 respectively, to enable reagents and sample material to flow into and out of the column C6.

FIG. 2 shows all six columns in elevation and it can be seen that movement of lever 108 causes all six columns to be urged into sealing contact with respective O-rings simultaneously.

Heating of Samples

The sample or samples being analysed in the instrument are placed in reaction vessels 60, 61 and are heated in these reaction vessels in the presence of reagents, all as described above.

Figure 5:
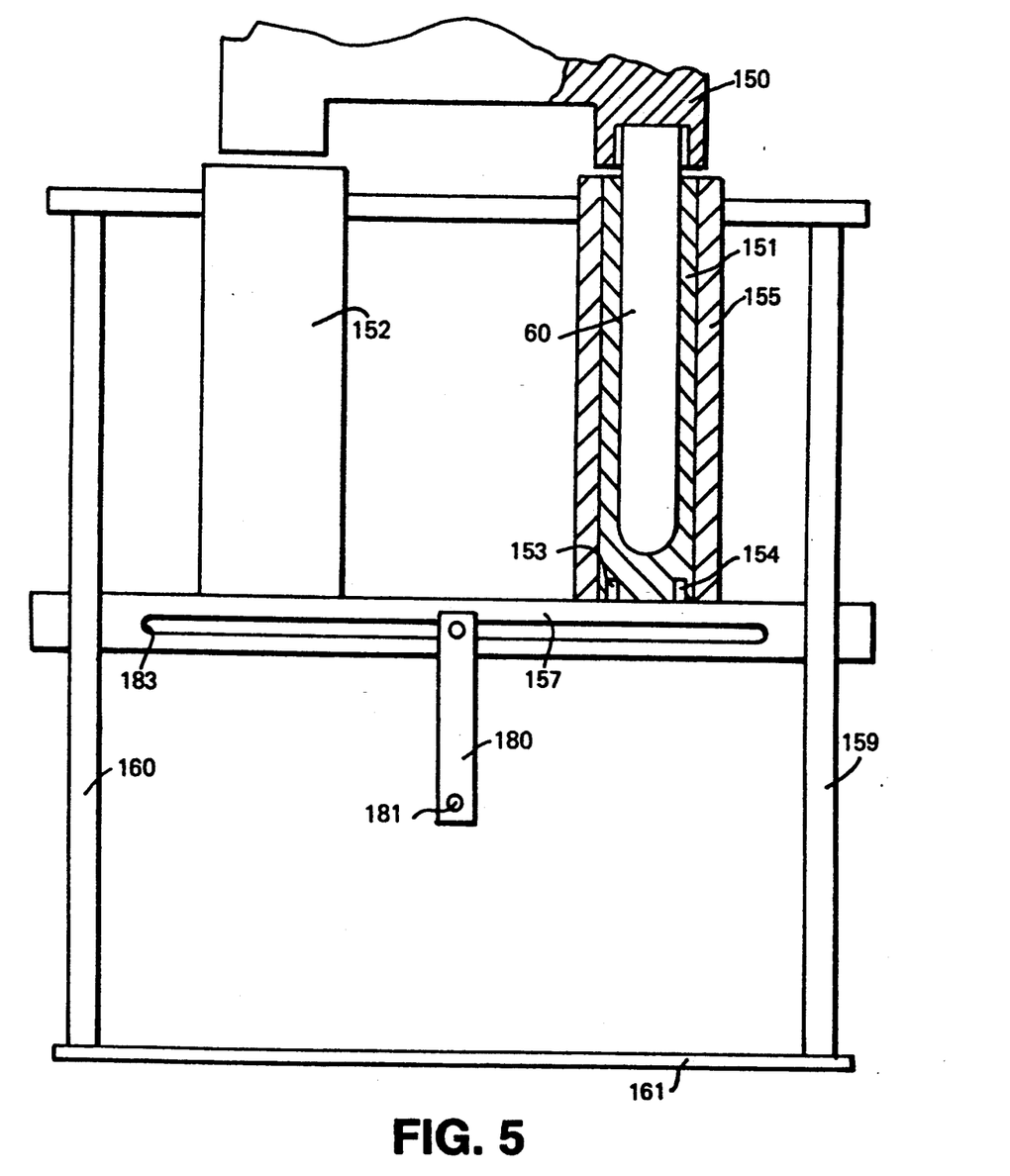
FIG. 5 is a scrap view of the heater assemblies of the apparatus.
Figure 6:
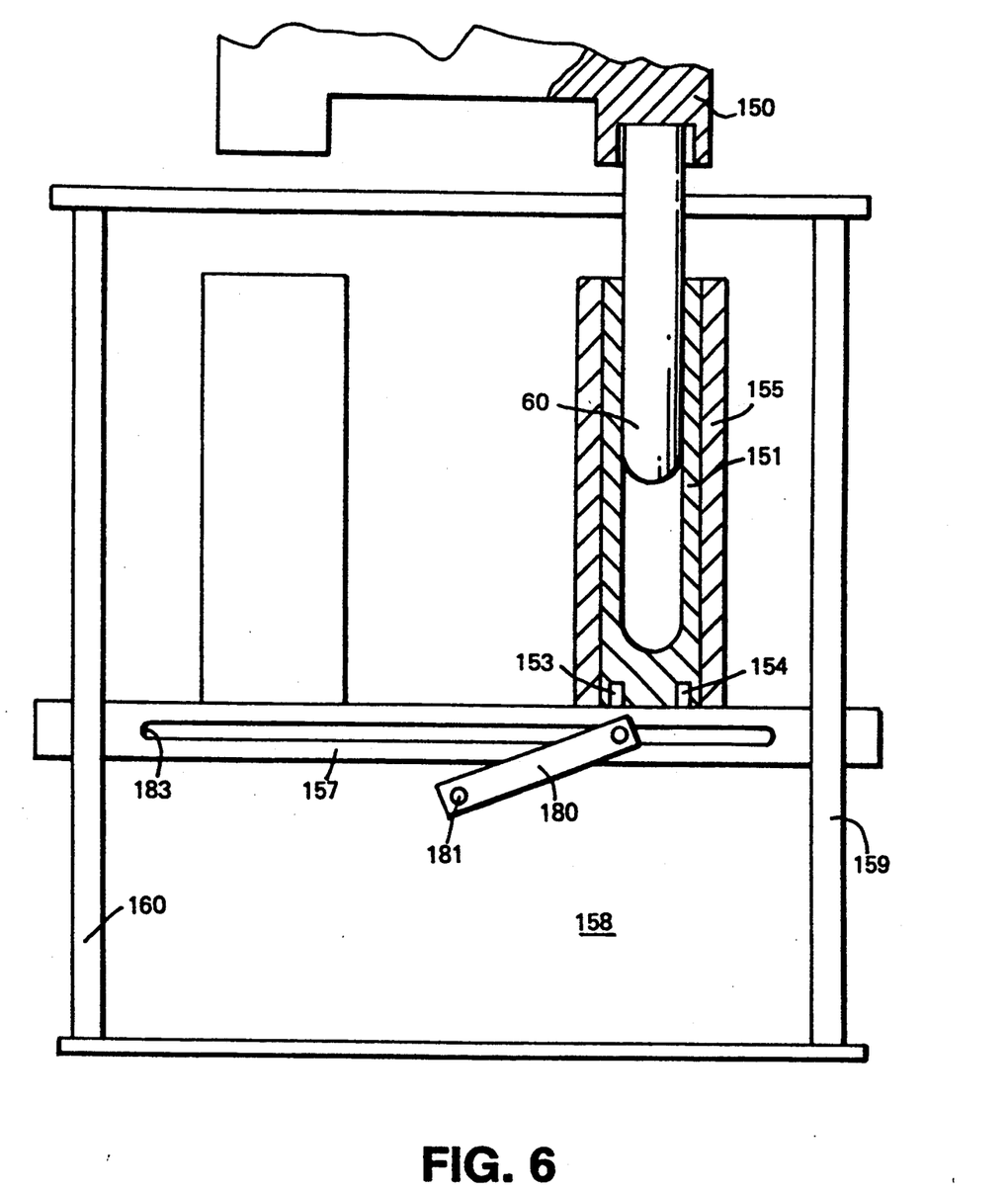
FIG. 6 is the same view as FIG. 5, but with the heaters partly lowered.

FIGS. 5 and 6 show the assembly for carrying out the heating cycles. Reaction vessel 60, when loaded with sample material, is screwed into a holder 150, in which position a heating assembly 151 can be raised, under control of the system controller, to surround the reaction vessel, as shown in FIG. 5. There is a separate heating assembly 151, 152 for each reaction vessel, with the assembly 151, on the right of the Figure, being shown in cross-section. FIGS. 5 and 6 only show one reaction vessel (60) in use.

Heating assembly 151 comprises an electrical heating element 153 and a temperature sensor 154; assembly 151 surrounds the reaction vessel 60 and conducts heat from element 153 so as to heat the reaction vessel 60. Assembly 151 is surrounded by a cylindrical insulator 155. The two heating assemblies are mounted on a platform 157 which can be raised and lowered on pillars 159 and 160.

Figure 7:
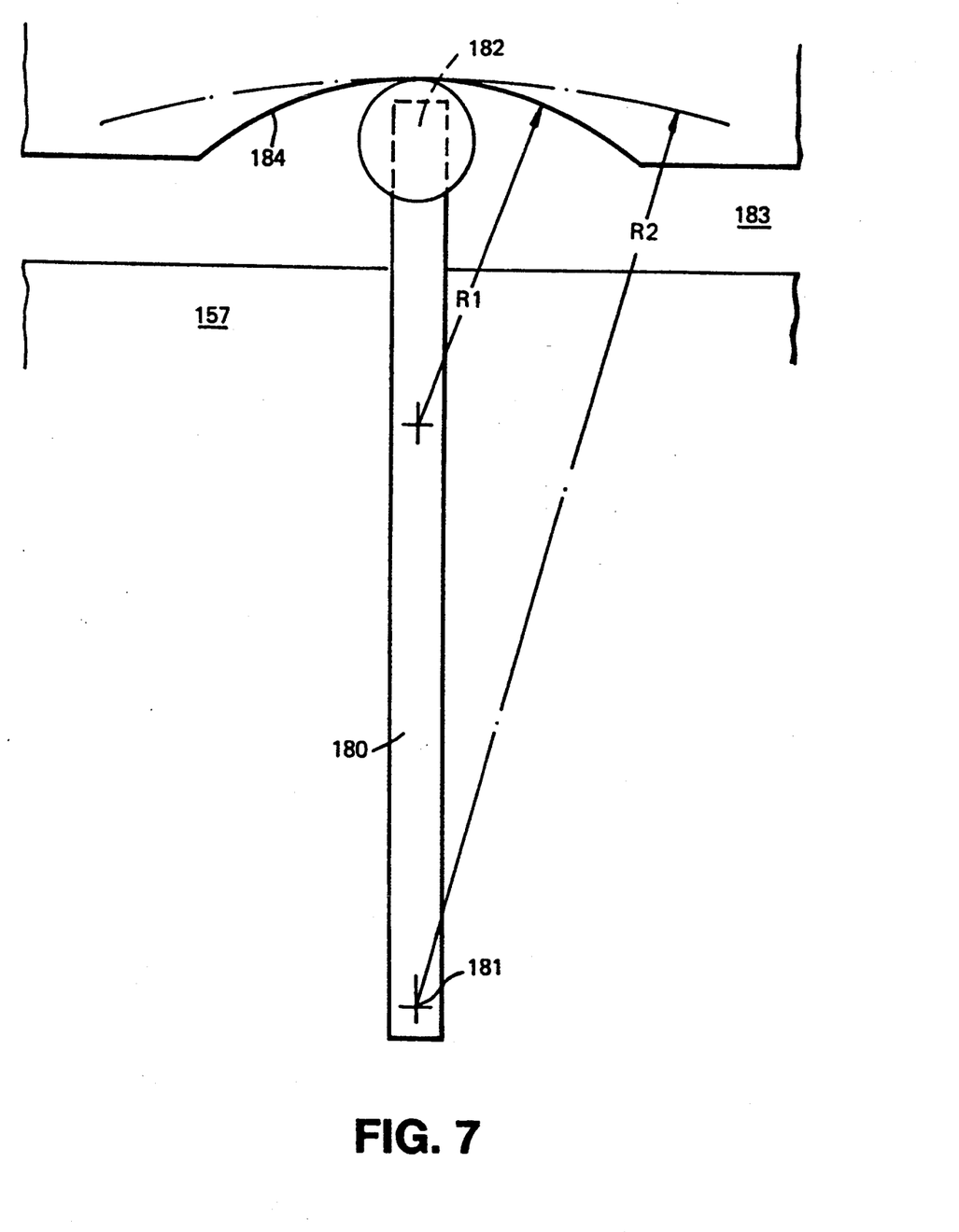
FIG. 7 is a diagram of the mechanism for raising and lowering the heater assemblies.

In FIG. 6, the heater assembly is shown partly raised/lowered. The platform 157 can be moved up and down by rotation of a crank arm 180 about a pivot 181. As shown in FIG. 7, arm 180 has a roller 182 at its end, engaging in an elongate slot 183 in platform 157, and 360° rotation of the crank arm 180 causes the platform to be raised and lowered.

When the crank arm 180 is rotated to raise the heating assembly and keep it there, it is very difficult to ensure that the arm stops exactly in the vertical position, i.e. to prevent its tendency to wander away from the vertical under the influence of vibration or any movement of the instrument. This would allow the heater assembly to lower under its own weight.

To ensure that the crank arm 180 is held stably in the upright position, the arrangement shown in FIG. 7 is used. The slot 183 in platform 157 has a slight recess 184 in its upper surface at the top dead centre position. As the arm 180 approaches top dead centre just as roller 182 enters recess 184, it actuates detectors (not shown) which stop the drive to arm 180. Because the radius, R1, of recess 184 is less than the radius, R2, of rotation of arm 180, once roller 182 has entered recess 184 it will be forced to the centre of the recess. Because roller 182 is fixed to arm 180, it can only move along radius 2, whilst the shape of recess 184 confines the movement of roller 182 to the radius R1. Thus, the roller will always move to the top dead centre and any vibration or movement of the instrument will only help to centralise the roller. The arm 180 will be held stably in the upright position.

The width of the recess 184 is dependent on the inertia of the assembly driving the arm 180 and the tolerances of the detectors to ensure that the arm can always stop in the recess 184.

It will easily be understood that, whilst the specific arrangement now described raises the heater to surround the vessel, it can be arranged for the relative movement between the heater and the vessel to be caused by moving either.

Reaction Vessel

Figure 8:
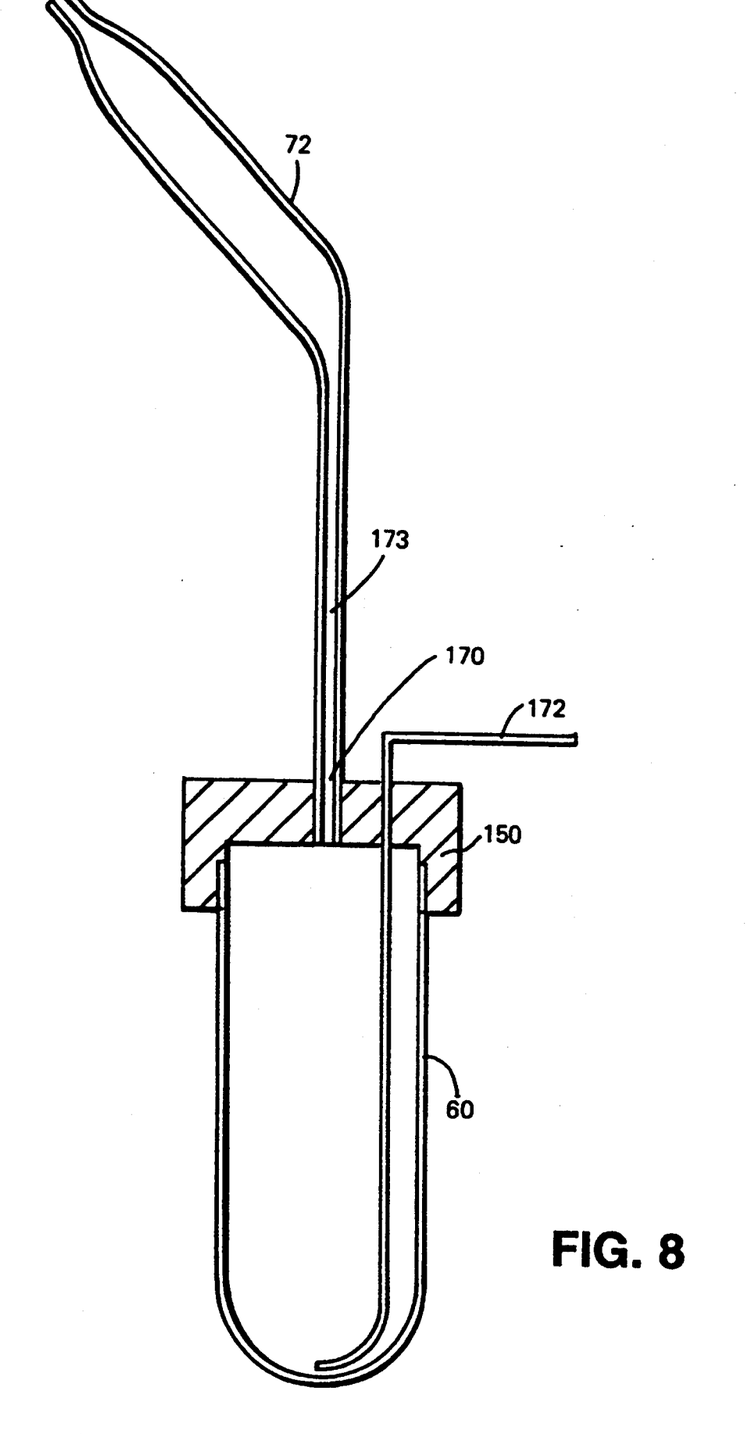
FIG. 8 is a scrap view of an overflow assembly for a holding vessel of apparatus of the invention.

In the course of performing reactions on the samples, various reagents are delivered to the reaction/holding vessels, and it is essential then at various times in the processes for the reagent and sample material to be completely removed from the reaction vessels. It has been found that simply filling the reaction vessels with rinsing liquid does not guarantee complete removal of contaminants. To wash the reaction/reaction vessel 60 thoroughly, it is filled to its top with a washing reagent. Argon is then injected through line 5 172 and this causes argon and liquid to be forced into overflow vessel 72. However, because vessel 72 is inclined at an angle, the liquid forced into this vessel does not pass out of its top but drains back down into vessel 60. The liquid is then removed through line 172 to waste.

Liquid Mixing

At several points in the process, it is required to agitate the contents of the reaction/holding vessel, either to homogenise a two-phase system, or to ensure the sides of the vessel are optimally cleaned. This is effected by opening a path from the inert gas source to the vessel, initially with the valve to the vessel closed.

Alternative Embodiment

Figure 9:
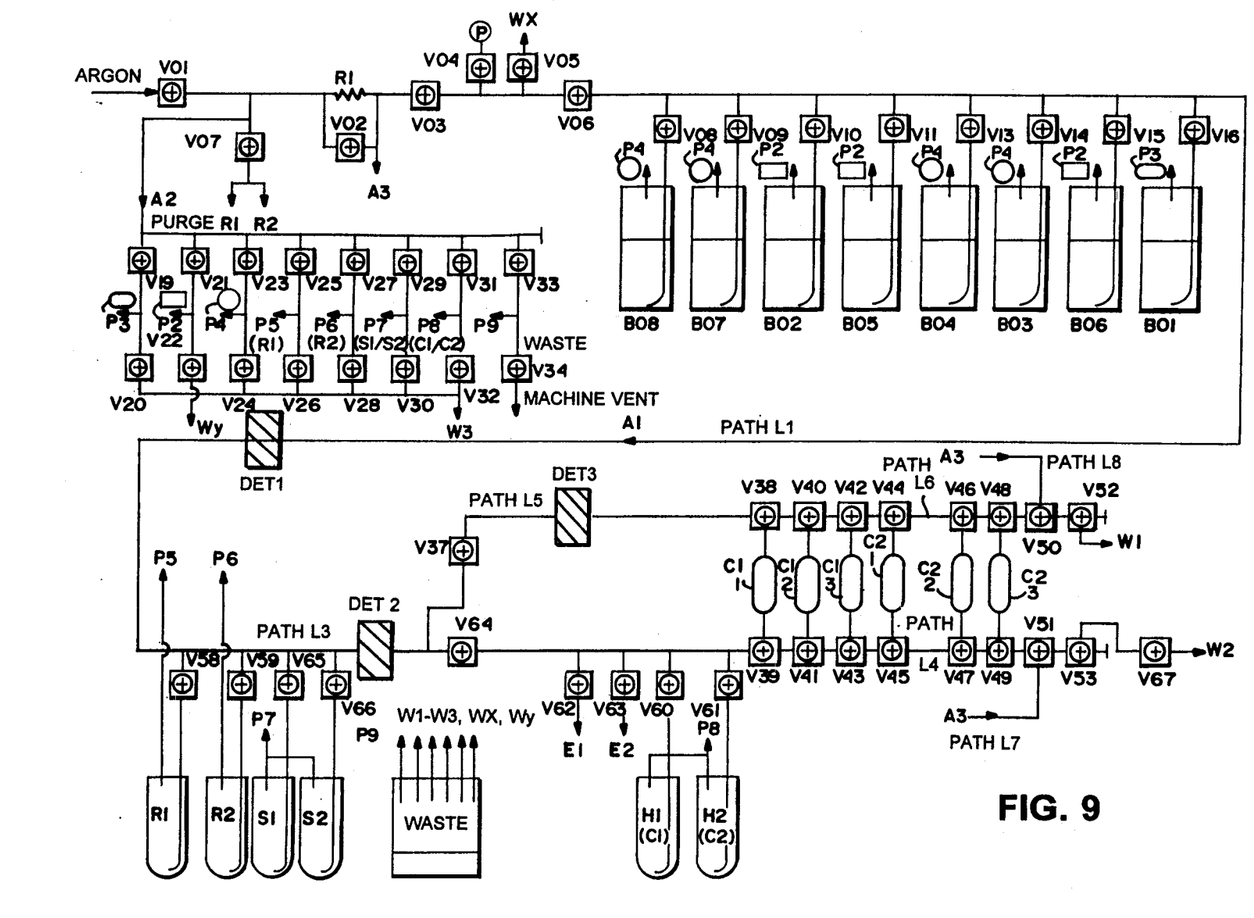
FIG. 9 is a diagram of another embodiment of the invention.

The "Detailed Description of the Invention given above is with respect to the apparatus shown in FIG. 1. An alternative embodiment of the invention is shown in FIG. 9. In many respects, operation of the embodiment of FIG. 9 is parallel to that of FIG. 1, and indeed an understanding of the operation of the former will facilitate understanding of the latter.

FIG. 9 shows an argon source (ARGON) to a reaction line via a valve V01, and also a pressure input P via a valve V04. The line comprises purge exits R1 and R2, waste exits W1-W3, Wx and Wy to a waste chamber (WASTE) with a pressurised outlet P9. The line also has a machine vent and product outlets E1 and E2.

A1 indicates the path L1 along which reactants from chambers B01-B08 can selectively be passed. It will be readily apparent that valves V01-V34 can be controlled, as desired, to cause purging or the introduction of reactants. The flow of reactants along the path L1 is determined by flow detector DET1. Reactants can be selectively introduced into reaction chambers R1, R2, or S1, S2, or can be passed along path L3, via flow detector DET2, and then along path L5, via flow detector DET3, to any of chromatographic columns C1, C2 and C3. After chromatographic separation, products can be re-circulated between reaction vessels R1, R2, S1, S2 and H1, H2 via paths L3, L4 and L5-C(1,2,3)-L4.

Paths L4, L7 and L8 allow pressure to be applied to the downstream side of the fluid path, enabling maximimal recovery of liquid passed along paths L6 and L4.

The invention has been described in terms of particular embodiments, but is not restricted thereto. Alternatives other than those described above will be apparent to the skilled reader.

What we claim is:

1. Apparatus comprising:
    a source of inert gas;
    a line into which the inert gas can pass, under pressure, to a plurality of outlets, the line being sealed with respect to the atmosphere; and
    in successive connection with the line via appropriate valves;
    a plurality of vessels for liquid reactants that can be introduced into the line by selective direction of the inert gas therethrough; and
    at least one reaction chamber into which said liquid reactants can be selectively directed and from which reaction products can pass along the line;
    at least one liquid flow detector selected from a first liquid flow detector for detecting liquid flow in the line between said vessels and said at least one reaction chamber, and a second liquid flow detector for detecting liquid flow between said at least one reaction chamber and one or more of said outlets;
    at least one column through which said reactants or said reaction products can be selectively directed and either returned to said at least one reaction chamber or passed to at least one of said outlets.

2. Apparatus as claimed in claim 1, which comprises said first liquid flow detector and said second liquid flow detector.

3. Apparatus as claimed in claim 1, wherein said second liquid flow detector is for detecting liquid flow between said at least one reaction chamber and said at least one column.

4. Apparatus as claimed in claim 1, further including a temperature controller arranged to control the temperature of said at least one reaction chamber within a range of non-ambient temperatures and to control the rate of change of temperature of the reaction vessel.

5. Apparatus as claimed in claim 4, further comprising means for heating said at least one reaction chamber and means for causing relative movement such that said heating means surrounds and encloses said at least one reaction chamber during the temperature control process and for automatically reversing said relative movement, in use of the apparatus.

6. Apparatus as claimed in claim 5, further including an over-centre mechanism for ensuring positive retention of the heating means when raised to surround said at least one reaction chamber.

7. Apparatus as claimed in claim 1, further including means for the pressurisation and ventilation of said at least one reaction chamber.

8. Apparatus comprising:
    a source of inert gas;
    a line into which the inert gas can pass, under pressure, to a plurality of outlets, the line being sealed with respect to the atmosphere; and
    in successive connection with the line via appropriate valves;
    a plurality of vessels for liquid reactants that can be introduced into the line by selective direction of the inert gas therethrough; and
    a plurality of reaction chambers into which said liquid reactants can be selectively directed and from which reaction products can pass along said line;
    at least one liquid flow detector selected from a first liquid flow detector for detecting liquid flow in the line between said vessels and said reaction chambers, and a second liquid flow detector for detecting liquid flow between said reaction chambers and one or more of said outlets; and
    at least one column through which said reactants or said reaction products can be selectively directed and means for returning the reaction products selectively to said reaction chambers or to at least one of said outlets.

9. Apparatus as claimed in claim 8, which comprises said first liquid flow detector and said second liquid flow detector.

10. Apparatus as claimed in claim 8, wherein said second liquid flow detector is for detecting liquid flow between said reaction chambers and said at least one column.

11. Apparatus as claimed in claim 8, further including a temperature controller arranged to control the temperature of said reaction chambers within a range of non-ambient temperatures and to control the rate of change of temperature of the reaction chambers.

12. Apparatus as claimed in claim 11, further comprising means for heating said chambers and means for causing relative movement such that said heating means surrounds and encloses said chambers during the temperature control process and for automatically reversing said relative movement, in use of the apparatus.

13. Apparatus as claimed in claim 12, further including over-center mechanisms for ensuring positive retention of the heating means when raised to surround said chambers.

14. Apparatus according to claim 8, further including means for the pressurization and ventilation of said chambers.

* * * * *